US00PP09118P

United States Patent [19]

Petersen

[11] Patent Number: Plant 9,118

[45] Date of Patent: Apr. 25, 1995

[54] DIPLADENIA PLANT NAMED 'CERISE'

[75] Inventor: Jens Petersen, Odense SV, Denmark

[73] Assignee: Weidners' Gardens, Inc., Encinitas, Calif.

[21] Appl. No.: 193,764

[22] Filed: Feb. 8, 1994

[51] Int. Cl.[6] ..... A01H 5/00

[52] U.S. Cl. ..... Plt./54.1

[58] Field of Search ..... Plt. 54.1

*Primary Examiner*—James R. Feyrer

[57] ABSTRACT

A distinct cultivar of Dipladenia plant named Cerise, characterized by its distinctive deep red flower color and dark green foliage and stems.

1 Drawing Sheet

The present invention relates to a new and distinctive cultivar of Dipladenia plant, botanically known as *Mandevilla sanderi* (Hemsl.), and in the trade as Dipladenia, and referred to be the cultivar name Cerise, and marketed by Weidners' Gardens, Inc., of Encinitas, Calif., under the Scarlet Pimpernel trademark. The new cultivar is a color mutation from the nonpatented Dipladenia cultivar Red Riding Hood, also known as Dark Dipladenia. The new cultivar was selected by me in Odense, Denmark, from a number of naturally-occurring mutants from Dipladenia cultivar Red Riding Hood.

Asexual reproduction of the new cultivar by single leaf node cuttings has shown that the unique features of this new Dipladenia are stabilized and are reproduced true to type in successive propagations. The plant was first asexually propagated by rooting single leaf nopde cuttings at my facilities in Odense, Denmark.

The new cultivar has not been observed under all possible environmental conditions. The phenotype may vary significantly with variations in environment such as temperature, light intensity and daylength. The following observations, measurements, values, and comparisons describe plants grown at Redlands Greenhouses Holdings Pty Ltd, Redland Bay, Queensland, Australia, and Weidners' Gardens, Inc., Encinitas, Calif., USA, under commercial greenhouse conditions.

The following characteristics have been repeatedly observed and are determined to be basic characteristics of Cerise, which in combination distinguish this Dipladenia as a new and distinct cultivar:

1. The distinctive deep red color of the flowers.
2. The distinctive dark green leaf color.

The new cultivar is most similar to the nonpatented Dipladenia cultivars Red Riding Hood and *Mandevilla sanderi* in its bushy to upright climbing habit, and continuous flowering under subtropical conditions. A comparison of the principal characteristics of those varieties with Cerise appears in Chart A attached hereto. The numbers and values appearing in Chart A are based on examination of twenty randomly-selected plants from plots of 750 plants for each variety. The mean, range and standard deviation are presented for all quantitative data.

Cerise is principally distinguished from Red Riding Hood and *Mandevilla sanderi* in its deep red flower color in contrast to the dark pink flower color of Red Riding Hood and the medium pink flower color of *Mandevilla sanderi.* Typically flower size of Cerise is smaller and fused corolla length is shorter than Red Riding Hood and *Mandevilla sanderi.* Cerise is also distinguished from Red Riding Hood and *Mandevilla sanderi* by its darker green leaves and stems.

The accompanying colored photographs illustrate the overall appearance and flower color of the new cultivar, showing the colors as true as it is reasonable possible to obtain in colored reproductions of this type.

The first photograph shows a single plant of Cerise compared to Red Riding Hood. The flowers of both plants are mature and demonstrate the faded flower color.

The second photograph shows a younger individual flower of Cerise with fully opened corolla.

The following is a detailed description of my new cultivar based on plants produced under normal commercial practice in Queensland, Australia, and Encinitas, Calif., USA, under greenhouse conditions with average day temperatures ranging from 22° to 30° C. and average night temperatures ranging from 16° to 20° C.

Color references are made to The Royal Horticultural Society Colour Chart except where general terms of ordinary dictionary significance are used.

Botanical classification: *Mandevilla sanderi* (Hemsl.) cv. Cerise.

Parentage: Naturally-occurring color mutant of Dipladenia cultivar Red Riding Hood.

Propagation:

A. *Type.*—By single leaf node cuttings.

B. *Time to initiate roots.*—42 to 56 days at temperatures of 15° to 28° C.

C. *Rooting habit.*—Fibrous, branching.

Plant description:

A. *General appearance.*—Bush to upright climbing perennial which flowers continuously under warm (higher than 18°) night temperatures. Foliage cover is medium to dense. Stems are waxy. Flowers are abundant with fused yellow-throated corolla that is funnelform and five-parted.

B. *Foliage and stem description.*—Leaf shape and size: Numerous; opposite arrangement; pinnately veined; broadly oblong-elliptic; apex acuminate; base rounded; entire margins; on average, 4.5 cm wide by 6 cm long; petioles are long, 6 to 12 mm; leaf morphology does not change with maturity. Leaf texture: Top and bottom sides glabrous. Leaf color: Young foliage top side: 147A with red (46A) overtones. Young foliage under side: 46A. Mature foliage top side: 147A. Mature foliage under side: 146C. Vein color: 46A. Stem color: Stem tip: 141C. Stem, 4 to 5 leaves below tip: 144A. Stem, 12 to 13 leaves below tip: 199C.

Flowering description:

A. *Flowering habit.*—Inflorescence arranged as a lateral raceme.

B. *Natural flowering season.*—Under subtropical conditions, year-round flowering.

C. *Quantity of flowers.*—Numerous inflorescences per plant, usually 4 to 7 flowers per axil.

D. *Flowers.*—Shape: Funnelform corolla, five-parted calyx. Size: Average flower diameter of 67.5 mm, average length of fused corolla is 62 mm. Peduncle color: 46A. Corolla color: Flower bud: During development, color changes from 46A, progressively becoming lighter with age to 46B, with mature bud color, 45A. Corolla when opening: 45A. Fully open corolla: Top side: 45A. Bottom side: 57A. Corolla fading to: 57A then to 57D. Inside throat: 14B. Inside throat fading to: 9A.

E. *Reproductive organs.*—Stamens: Enclosed within throat, anthers connivent. Seed: Normally absent, flowers are nearly sterile.

Disease resistance: No resistance nor susceptibility to diseases have been observed.

CHART A

| Characteristic | Cerise | Red Riding Hood | *Mandevilla sanderi* |
|---|---|---|---|
| Corolla color | red 45A | dark pink 57C | pink 55B |
| Corolla throat color | 14B | 15A | 14A |
| Flower diameter | | | |
| mean | 67.5 mm | 75 mm | 74 mm |
| range | 60–74 | 68–80 | 71–81 |
| std. dev. | 4.5 | 3.5 | 4 |
| Fused corolla length | | | |
| mean | 62 mm | 74.5 mm | 70 mm |
| range | 52.5–80 | 62–88 | 62–84 |
| std. dev. | 9.5 | 7 | 6.5 |
| Leaf color | 147A | 141B | 141B |
| Leaf length | | | |
| mean | 58 mm | 67.5 mm | 61.5 mm |
| range | 46–69 | 53–78 | 54–68 |
| std. dev. | 6 | 6 | 14 |
| Leaf width | | | |
| mean | 44 mm | 43 mm | 40 mm |
| range | 34–52 | 39–50.5 | 36–47 |
| std. dev. | 5.5 | 9 | 9 |
| Petiole length | | | |
| mean | 9.5 mm | 7.5 mm | 7 mm |
| range | 6–12 | 5.5–9 | 5–9 |
| std. dev. | 2 | 1 | 1.5 |
| Stem color | | | |
| tip | 144C | 144B | 144B |
| 4–5 leaves below tip | 144A | 144B | 144C |
| 12–13 leaves below tip | 199C | 165B | 164A |

I claim:

1. A new and distinct Dipladenia plant named Cerise, as illustrated and described.

* * * * *

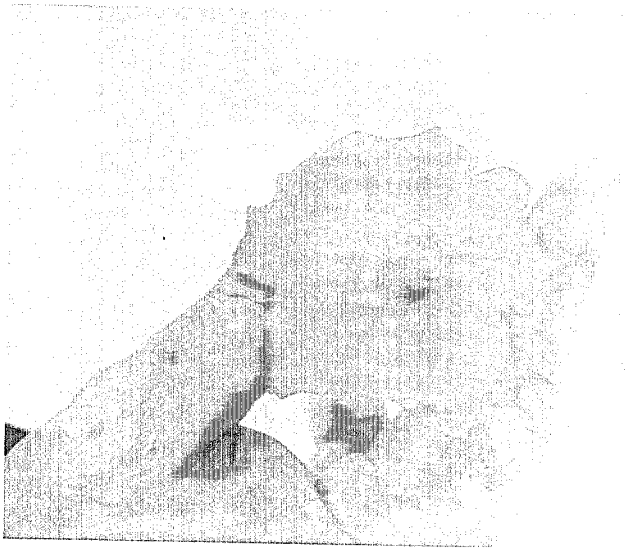

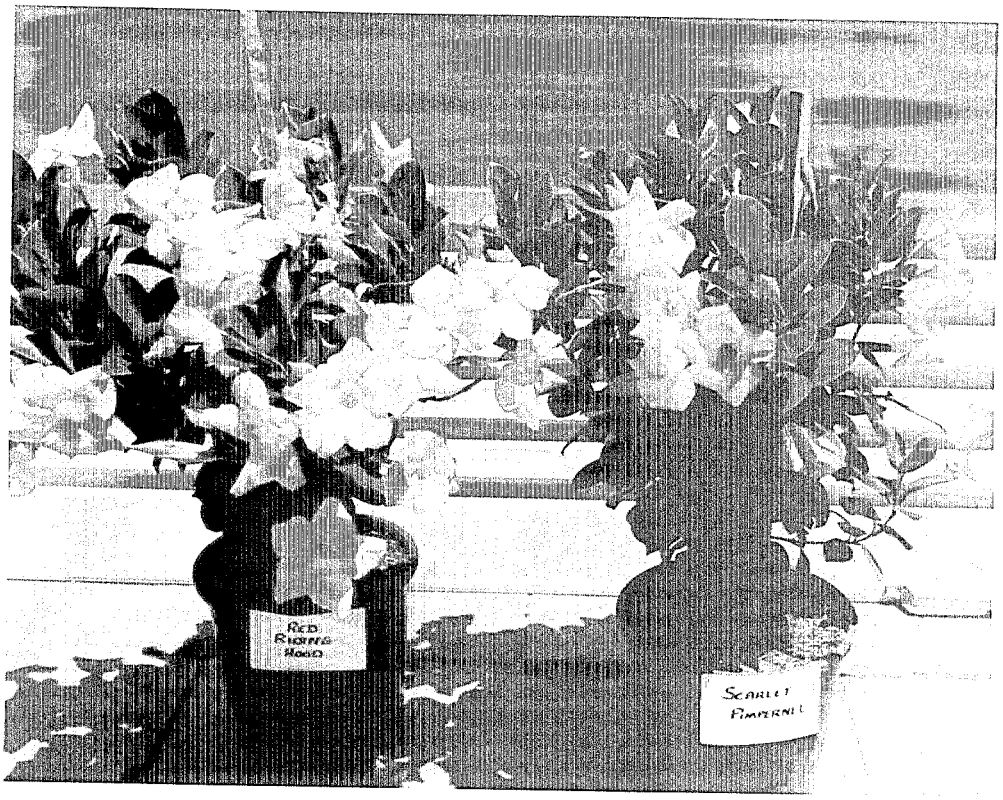
RED
RHONA
ROSA
SCARLET
PIMPERNEL